United States Patent [19]
Dolman et al.

[11] Patent Number: 4,889,863
[45] Date of Patent: Dec. 26, 1989

[54] NEW THIAZOLE COMPOUNDS HAVING FUNGICIDAL ACTIVITY

[75] Inventors: Hendrik Dolman; Johannes Kuipers, both of Weesp, Netherlands

[73] Assignee: Duphar International Research B.V., Weesp, Netherlands

[21] Appl. No.: 222,907

[22] Filed: Jul. 22, 1988

[30] Foreign Application Priority Data

Jul. 27, 1987 [NL] Netherlands ............... 8701764

[51] Int. Cl.⁴ .............. C07D 277/36; C07D 277/56; A01N 43/78
[52] U.S. Cl. ................................ 514/312; 514/369; 546/153; 548/184; 548/185; 548/186; 548/187; 548/188
[58] Field of Search ............ 548/186, 187, 188, 184, 548/185; 546/153; 514/269, 312

[56] References Cited

U.S. PATENT DOCUMENTS 4,077,968  3/1978  Maeda ..................... 548/187

FOREIGN PATENT DOCUMENTS 2098203 11/1982 United Kingdom ............. 548/189

*Primary Examiner*—Robert Gerstl
*Attorney, Agent, or Firm*—Stevens, Davis, Miller & Mosher

[57] ABSTRACT

The invention relates to new thiazole compounds of the general formula

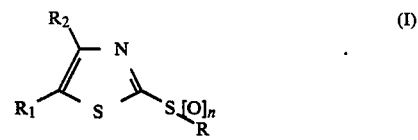

wherein
  R is an $C_1$-$C_{12}$ alkyl group or a phenyl group, which groups are unsubstituted or substituted with halogen, nitro or cyano;
  $R_1$ is a cyano group; a formyl group; an alkylcarbonyl or alkoxycarbonyl group having 2–5 carbon atoms; or a substituted or non-substituted benzoyl group;
  $R_2$ is a hydrogen atom; a halogen atom; an amino group; an amino group substituted with 1 or 2 substituents selected from the group consisting of $C_1$-$C_4$ alkyl, $C_2$-$C_5$ alkynyl, $C_2$-$C_5$ alkylcarbonyl and $C_2$-$C_5$ alkoxycarbonyl; an alkyl, alkoxy, alkylthio, alkylsulphinyl or alkyl-sulphonyl group having 1–4 carbon atoms; or a substituted or non-substituted aryl, aryloxy, arylthio, arylsulphinyl or arylsulphonyl group; and
  n is 1 or 2.

The new compounds show a fungicidal activity and may be used in particular against plant pathogenic seed fungi and soil fungi.

9 Claims, No Drawings

NEW THIAZOLE COMPOUNDS HAVING FUNGICIDAL ACTIVITY

The invention relates to new thiazole compounds as well as to a method of preparing the said compounds. The invention furthermore relates to fungicidal compositions, and in particular to compositions for the treatment of soil or seed against phytophagous micro-organisms, which compositions comprise the new compounds as the active substances, and to the use of the said compositions in agriculture and horticulture.

Nitrothiazoles having fungicidal activity, for example, for the treatment of seeds, are known from German patent application Ser. No. (Offenlegungsschrift) 2,627,328. A compound described in this application is 2-methylsulphinyl-4-methyl-5-nitrothiazole. However, this compound has proved to be insufficiently active and to show phytotoxicity in practical eperiments, as will become apparent from the examples.

It is the object of the invention to provide new thiazole compounds having an improved fungicidal activity in particular against plant pathogenic seed and soil fungi, and having a decreased toxicity with respect to the crop. This object can be achieved by means of new thiazole compounds which are characterized according to the invention by the general formula

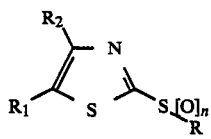
(I)

wherein

R is an $C_1$–$C_{12}$ alkyl group or a phenyl group, which groups are unsubstituted or substituted with halogen, nitro or cyano;

$R_1$ is a cyano group; a formyl group; an alkylcarbonyl or alkoxycarbonyl group having 2–5 carbon atoms; or a substituted or non-substituted benzoyl group;

$R_2$ is a hydrogen atom; a halogen atom; an amino group; an amino group substituted with 1 or 2 substituents selected from the group consisting of $C_1$–$C_4$ alkyl, $C_2$–$C_5$ alkynyl, $C_2$–$C_5$ alkylcarbonyl and $C_2$–$C_5$ alkoxycarbonyl; an alkyl, alkoxy, alkylthio, alkylsulphinyl or alkylsulphonyl group having 1–4 carbon atoms; or a substituted or non-substituted aryl, aryloxy, arylthio, arylsulphinyl or arylsulphonyl group; and n is 1 or 2.

Where a substituted phenyl group is mentioned hereinbefore, the phenyl group is substituted with one or more substituents selected from the group consisting of halogen, nitro, cyano, $C_1$–$C_4$ alkyl, $C_1$–$C_4$ haloalkyl, $C_1$–$C_4$ alkoxy, $C_1$–$C_4$ haloalkoxy and $C_1$–$C_4$ alkylsulphonyl.

An aryl group is to be understood to mean herein not only a phenyl group, but also a heteroaryl group such as pyridyl and quinolyl.

Of the above-mentioned compounds are to be preferred thiazole compounds of the general formula

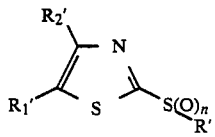
(II)

wherein

R' is an alkyl group having 1–6 carbon atoms,
$R_1'$ is a cyano group or an acetyl group,
$R_2'$ is a hydrogen atom, a halogen atom, an amino group, or an amino group substituted with 1 or 2 substituents selected from the group consisting of $C_1$–$C_4$ alkyl, $C_2$–$C_5$ alkylcarbonyl and $C_2$–$C_5$ alkoxycarbonyl, and
n is 1 or 2.

Examples of new thiazole compounds according to the invention are:

(1) 2-methylsulphonyl-4-amino-5-cyanothiazole,
(2) 2-methylsulphinyl-4-amino-5-cyanothiazole,
(3) 2-ethylsulphonyl-4-amino-5-cyanothiazole,
(4) 2-n-propylsulphonyl-4-amino-5-cyanothiazole,
(5) 2-n-propylsulphinyl-4-amino-5-cyanothiazole,
(6) 2-n-butylsulphonyl-4-amino-5-cyanothiazole,
(7) 2-n-butylsulphinyl-4-amino-5-cyanothiazole,
(8) 2-n-hexylsulphonyl-4-amino-5-cyanothiazole,
(9) 2-n-hexylsulphinyl-4-amino-5-cyanothiazole,
(10) 2-methylsulphonyl-5-cyanothiazole,
(11) 2-methylsulphinyl-5-cyanothiazole,
(12) 2-ethylsulphonyl-5-cyanothiazole,
(13) 2-ethylsulphinyl-5-cyanothiazole,
(14) 2-n-propylsulphonyl-5-cyanothiazole,
(15) 2-n-propylsulphinyl-5-cyanothiazole,
(16) 2-n-butylsulphonyl-5-cyanothiazole,
(17) 2-n-butylsulphinyl-5-cyanothiazole,
(18) 2-methylsulphinyl-4-chloro-5-cyanothiazole,
(19) 2-ethylsulphonyl-4-chloro-5-cyanothiazole,
(20) 2-ethylsulphinyl-4-cloro-5-cyanothiazole,
(21) 2-n-propylsulphonyl-4-chloro-5-cyanothiazole,
(22) 2-n-propylsulphinyl-4-chloro-5-cyanothiazole,
(23) 2-n-butylsulphonyl-4-chloro-5-cyanothiazole,
(24) 2-n-butylsulphinyl-4-chloro-5-cyanothiazole,
(25) 2-ethylsulphonyl-4-N-methoxycarbonylamino-5-cyanothiazole,
(26) 2-ethylsulphonyl-4-(N-methyl-N-methoxycarbonylamino)-5-cyanothiazole,
(27) 2-n-butylsulphonyl-4-N-acetylamino-5-cyanothiazole,
(28) 2-n-butylsulphinyl-4-N-acetylamino-5-cyanothiazole,
(29) 2-n-butylsulphinyl-4-(N-methyl-N-acetylamino)-5-cyanothiazole,
(30) 2-ethylsulphonyl-4-amino-5-acetylthiazole,
(31) 2-n-butylsulphonyl-4-amino-5-acetylthiazole,
(32) 2-n-butylsulphinyl-4-amino-5-acetylthiazole,
(33) 2-n-hexylsulphonyl-4-amino-5-acetylthiazole,
(34) 2-n-hexylsulphinyl-4-amino-5-acetylthiazole,
(35) 2-n-butylsulphonyl-4-phenoxy-5-cyanothiazole,
(36) 2-n-propylsulphonyl-4-phenylsulphonyl-5-cyanothiazole,
(37) 2-cyanomethylsulphinyl-4-amino-5-cyanothiazole,
(38) 2-n-butylsulphinyl-4-amino-5-benzoylthiazole,
(39) 2-n-hexylsulphinyl-4-chloro-5-benzoylthiazole,
(40) 2-methylsulphinyl-4-N-acetylamino-5-cyanothiazole,
(41) 2-methylsulphonyl-4-chloro-5-cyanothiazole,
(42) 2-phenylsulphonyl-4-amino-5-cyanothiazole,

(43) 2-phenylsulphinyl-4-amino-5-cyanothiazole,
(44) 2-ethylsulphinyl-4-amino-5-acetylthiazole,
(45) 2-n-butylsulphonyl-4-methoxy-5-cyanothiazole,
(46) 2-n-butylsulphinyl-4-(N-methyl-N-acetylamino)-5-cyanothiazole,
(47) 2-n-butylsulphinyl-4-chloro-5-acetylthiazole,
(48) 2-n-butylsulphonyl-4-chloro-5-acetylthiazole,
(49) 2-n-butylsulphinyl-5-acetylthiazole,
(50) 2-n-butylsulphonyl-5-acetylthiazole,
(51) 2-n-butylsulphinyl-4-amino-5-benzoylthiazole,
(52) 2-n-butylsulphinyl-4-chloro-5-benzoylthiazole,
(53) 2-n-butylsulphonyl-4-chloro-5-benzoylthiazole,
(54) 2-n-butylsulphinyl-5-benzoylthiazole,
(55) 2-n-butylsulphonyl-5-benzoylthiazole,
(56) 2-n-butylsulphonyl-4-N-acetylamino-5-acetylthiazole,
(57) 2-methylsulphinyl-4-(8-quinolyloxy)-5-cyanothiazole,
(58) 2-methylsulphinyl-4-chloro-5-formylthiazole,
(59) 2-methylsulphinyl-5-formylthiazole,
(60) 2-n-propylsulphinyl-4-(N-acetyl-N-propargylamino)-5-cyanothiazole, and
(61) 2-phenylsulphonyl-4-chloro-5-cyanothiazole.

The new compounds according to the invention show a strong fungicidal activity with respect to a wide spectrum of pathogenic fungi which may occur in agricultural and horticultural crops.

The compounds according to the invention may be used against so-called air-borne, soil-borne and seed-borne pathogens. Examples of air-borne pathogenic fungi are *Uromyces phaseoli* and *Phytophthora infestans*.

It has been found that the new compounds according to the invention are particularly active against soil-borne and seed-borne pathogenic micro-organisms, i.e. against phytophagous soil fungi ("soil-borne diseases"), for example, Pythium spp. (for example, *Pythium ultimum* and *Pythium splendens*) and *Rhizoctonia solani*, against *phytophagous fungi* which are seed-borne ("seed-borne diseases"), for example, *Pyrenophora graminea* on barley, *Tilletia caries* on wheat, Fusarium spp. (for example, *Fusarium nivale* and *Fusarium culmorum*) on wheat, *Leptosphaeria nodorum* on wheat and Ustilago spp. (for example, *Ustilago avenae*) on oats.

Infections with phytophagous fungi, e.g. phytophagous soil fungi or fungi which are seed-borne, can be prevented by treating the soil destined for planting or sowing, or, which will usually be preferred for economical reasons, the seed itself with a composition which comprises a new compound according to the invention.

For practical applications the substances in accordance with the invention are processed to compositions. In such compositions the active substance is mixed with solid carrier material or dissolved or dispersed in liquid carrier material, optionally in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersing powders, miscible oils, granules and pellets.

Dispersible powders, pastes and miscible oils are compositions in concentrate form which are diluted prior to or during use.

The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, optionally in the presence of a binder, on granular carrier material, for example porous granules (sand or ground marl), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and then glomulating the mixture to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution.

Suitable solvents are, for example, xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, a glycol ether or dimethyl formamide, to which solution a dispersing agent and, optionally a surface-active substance has been added. When diluting with water shortly before or during spraying, an aqueous dispersion of the active substance is then obtained.

An aerosol composition according to the invention is obtained in the usual manner by incorporating the active substance, optionally in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. composition which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the pesticide to the plant. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

Moreover leaf fertilisers may be present.

For use in such a combination composition are to be considered the following known insecticidal, acaricidal and fungicidal compounds.

Insecticides, for example:
1. organic chlorine compounds, for example: 6,7,8,9,10,-hexachloro-1,5,5a,6,9,9a-hexahydro-6,9-methano-2,4,3-benzo[e]-dioxathiepine-3-oxide;
2. carbamates, for example: 2-dimethylamino-5,6-dimethylpyrimidin-4-yl dimethyl carbamate and 2-isopropoxyphenyl methylcarbamate;
3. di(m)ethylphosphates, for example: 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethyl phosphate;
4. O,O-di(m)ethyl phosphorothioates, for example, O(S)-2-methylthioethyl-, S-2-ethylsulphinylethyl-, S-2-(1-methylcarbamoylethylthio)ethyl-, 0-4-bromo-2,5-dichlorophenyl-, 0-3,5,6-trichloro-2-pyridyl-, 0-2-isopropyl-5-methylpyrimidin-4-yl-, and 0-4-nitrophenyl O,O-di(m)ethyl phosphorothioate;
5. O,O-di(m)ethyl phosphorodithioates, for example, S-methylcarbamoylmethyl-, S-2-ethylthioethyl-, S-(3,4-dihydro-4oxobenzo[d]-1,2,3-triazin-3-ylmethyl)-, S-1,2-di-(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethyl phosphorodithioate;
6. phosphonates, for example, dimethyl 2,2,2-trichloro-1-hydroxyethyl phosphonate;
7. benzoylurea, for example, N-(2,6-difluorobenzoyl)-N'-(4-chlorophenyl)urea;
8. natural and synthetic pyrethroids;
9. amidines, for example, N'-2-(methyl-4-chlorophenyl)-N,N-dimethyl formamidine; and
10. microbial insecticides, such as Bacillus thuringiensis.

Acaricides, for example:
1. organic tin compounds, for example, tricyclohexyl tin hydroxide and di[tri-(2-methyl-2-phenyl-propyl)tin]-oxide;
2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone;

and furthermore: 3-chloro-ethoxyimino-2,6-dimethoxybenzyl benzoate and O,O-dimethyl S-methylcarbamoylmethyl phosphorothioate.

Fungicides, for example:
1. organic tin compounds, for example, triphenyltin hydroxide and triphenyltin acetate;
2. alkylene bisdithiocarbamates, for example, zinc ethylene bisdithiocarbamate and manganese ethylene bisdithiocarbamate;
3. 1-acyl- or 1-carbamoyl-N-benzimidazole(-2) carbamates and 1,2-bis(3-alkoxycarbonyl-2-thiureido)-benzene, and furthermore 2,4-dinitro-6-(2-acetylphenylcrotonate), 1-bis(dimethylamino)phosphoryl-3-phenyl-5amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidin-4-yl-dimethylsulphamate, 1-(4-chlorophenoxy)-3,3-dimethyl-1(1,2,4-triazol-1-yl)-2-butanone, 1-[2-(2,4-dichlorophenyl)-4-propyl-1,3-dioxolan-2-ylmethyl]-1H-1,2,4-triazole, 2,4'-difluoro-α-(1H-1,2,4-triazol-1-ylmethyl)benzhydryl alcohol, α-(2-chlorophenyl)-α-(4-fluorophenyl)-5-pyrimidinemethanol, α-(2-clorophenyl)-α-(4-chlorophenyl)-5-pyrimidinemethanol, 1-(isopropylcarbamoyl)-3-(3,5-dichlorophenyl)-hydantoin, N-(1,1,2,2-tetrachloroethylthio)-4-cyclohexene-1,2-carboximide, N-trichloromethylthio-4-cyclohexene-1,2-carboximide, N-tridecyl-2,6-dimethyl-morpholine, 5,6-dihydro-2-methyl-1,4-oxathiine-3-carboxanilide, 2,4,5-trimethyl-N-phenyl-3-furanecaboxamide, 2,5-dimethyl-N-cyclohexyl-N-methoxy-3-furanecarboxamide, and N-phenyl-2-methylfurane-3-carboxamide.

The dosages of the composition according to the invention desired for practical application will, of course, depend on various factors, for example, field of application, selected active substance, form of composition, nature and extent of the weeds and the weather conditions.

In general it holds that favourable results are achieved with a dosage which corresponds to 250–1000 g of the active substance per hectare.

When applied against phytophagous microorganisms good results are achieved when the soil is treated with a composition comprising an amount of active compound which corresponds to 2–100 kg of active substance per hectare. When applied to the seed itself, which is preferred for economical considerations, a dosage is preferred which corresponds to 100–1500 mg of active substance per kg of seed.

The new compounds according to the invention can be prepared as follows.

For example, the new thiazole compounds of the general formula

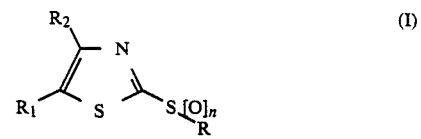

wherein

R, $R_1$, $R_2$ and n have the meanings given hereinbefore, can be prepared by reacting a compound of the general formula

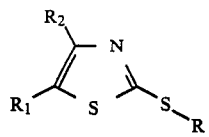

with an oxidant. Suitable oxidants are hydrogen peroxide and peroxycarboxylic acids, for example, performic acid, peracetic acid or a substituted perbenzoic acid, for example, p-nitroperbenzoic acid or m-chloroperbenzoic acid.

For the preparation of the sulphone, hydrogen peroxide is preferably used as an oxidant. When an equimolar quantity of peroxycarboxylic acid is used, for example, one of the above-mentioned percarboxylic acids, the sulphide can be oxidized selectively to the sulphoxide. These oxidation reactions are preferably carried out in a polar organic solvent, for example, formic acid, acetic acid, a ketone, for example acetone, or a chlorinated hydrocarbon, for example, methylene chloride. The reaction temperature depends on the reagents used and the selected solvent, and may vary between $-20°$ C. and the boiling-point of the solvent, preferably between $-10°$ C. and room temperature.

After the final product has been isolated, it may be purified, if desired, by recrystallisation or column chromatography.

Thiazoles to be used for the above oxidation reaction may be prepared as follows.

Compounds of the general formula

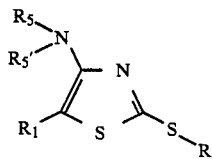

wherein

R and $R_1$ have the meanings given hereinbefore, and $R_5$ and $R_5'$ are equal or different and represent hydrogen atoms, $C_1-C_4$ alkyl groups, $C_2-C_5$ alkynyl groups, $C_2-C_5$ alkylcarbonyl groups or $C_2-C_5$ alkoxycarbonyl groups may be prepared by reacting a compound of the general formula

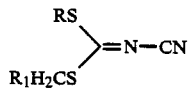

with a base, after which the amino group of the resulting compound of the general formula V, wherein $R_5$ and $R_5'$ are hydrogen atoms, may optionally be converted with a suitable alkylating or acylating agent. A suitable base for the cyclisation reaction is an alkali metal hydride or alkali metal hydroxide, for example, NaH, NaOH or KOH. This reaction is preferably carried out in a dipolar aprotic solvent, for example, DMF, at a temperature between $0°$ C. and the boiling-point of the solvent. As an alkylation agent may be used a suitable halide or sulphonate, or a dialkyl sulphate, preferably in the same solvent, preferably at slightly decreased temperature.

As an acylation agent may be used a suitable acyl halide, acid anhydride or pyrocarboxylic acid ester, preferably under the influence of a suitable catalyst, for example, an organic base such as 4-(N,N-dimethylamino)pyridine. Starting compound VI may be prepared according to the following reaction scheme:

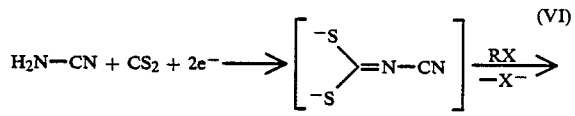

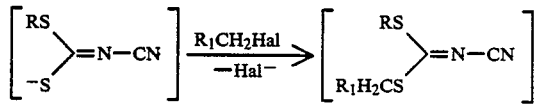

Compound (VI), as well as the other intermediate products placed in brackets, is usually not isolated but is immediately converted into the desired thiazole V by means of a base. In the above reactions, Hal is halogen, e.g. chlorine and X is halogen, sulphonate or sulphate. The first reaction step is preferably carried out in a polar solvent, for example, a dipolar aprotic solvent, such as, DMF, at decreased temperature. In the second reaction step a suitable alkylation agent is used, for example, a halide, sulphonate (e.g. tosylate or mesylate) or sulphate, under the same reaction conditions. The third reaction step is preferably carried out in the same solvent at a temperature between $0°$ C. and the boiling-point of the solvent.

Compound V, in which $R_5$ and $R_5'$ are hydrogen atoms, may alternatively be prepared via the following intermediates

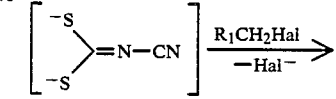

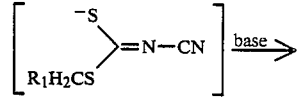

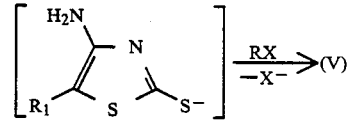

The 4-aminothiazoles thus obtained can be converted into thiazoles which are unsubstituted in the 4-position by reaction with an alkyl nitrite, preferably in a polar organic solvent, for example, a dipolar aprotic solvent such as DMF, preferably at elevated temperature, for example, between approximately $50°$ and $70°$ C. As an alkyl nitrite may be used, for example, isoamyl nitrite.

The above-mentioned 4-aminothiazoles can be converted into the corresponding 4-halothiazoles by reaction with an alkyl nitrite or a nitrite of an alkali metal, for example, sodium or potassium, in the presence of the desired halogen ions, for example, a hydrohalogenic acid or a metal halide, preferably an anhydrous cupric halide.

This reaction with a nitrite of an alkali metal is preferably carried out in a polar organic solvent, for example, methylene chloride or acetonitrile, if desired in a two-phase system with water or a saturated saline solution. A catalyst, for example, a metal halide, such as cuprous chloride, may optionally be added to stimulate the last mentioned conversion.

The reaction with an alkyl nitrite is the presence of an anhydrous metal halide is preferably carried out in a polar organic solvent, like acetonitrile. The 4-halothiazole compound is susceptible to substitution reactions in the 4-position, for example with alkanoles, alkyl mercaptans, hydroxy(hetero)aromates or mercapto(-hetero)aromates. In the last-mentioned conversions which may preferably take place under basic conditions in polar solvents, 4-alkoxythiazoles, 4-alkylthiothiazoles, 4-aryloxythiazoles of 4-arylthiothiazoles may be formed. The resulting thio compounds may again be oxidised in the manner described hereinbefore to the corresponding sulphinyl or sulphonyl compounds.

Thiazoles of the general formula

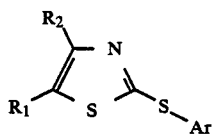

wherein the symbols $R_1$ and $R_2$ have the meanings given hereinbefore and Ar is a substitued or non-substituted phenyl group, can best be prepared by reacting a thiazole of the general formula

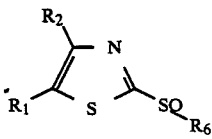

wherein the symbols $R_1$ and $R_2$ have the meanings given hereinbefore, and $R_6$ is an alkyl group having 1–6 carbon atoms, with a thiophenol of the general formula ArSH. This reaction is preferably carried out in a polar organic solvent, for example, acetonitrile, at a temperature between 0° C. and the boiling-point of the solvent. If desired, a quantity of an organic base, for example, an amine, such as triethylamine, can stimulate the conversion.

The invention will now be described in greater detail with reference to the ensuing specific examples.

EXAMPLE I

Preparation of 2-n-butylsulphinyl-5-cyanothiazole (17)

4.06 g of 85% m-chloroperbenzoic acid are gradually added at a temperature of 0°–5° C., while stirring, within 45 minutes, to a solution of 3.96 g of 2-n-butylthio-5-cyanothiazole in 100 ml of methylene chloride. After stirring for another 2 hours at 5° C. a saturated solution of sodium bicarbonate in approximately 50 ml of water is added; the reaction mixture is then stirred for 60 minutes. The organic layer is separated, washed with water and dried. After distilling off the solvent, the residue is taken up in approximately 100 ml of isopropanol. Upon cooling, the desired product crystallises. Sucking off, washing with petroleum ether (40–60) and drying: yield 3.57 g; melting-point 45°–48° C.; TLC: $R_f(CH_2Cl_2)$ 0.05.

The following compounds are prepared in a corresponding manner in which, if desired, p-nitroperbenzoic acid is used as an oxidizing agent and chloroform is used as a solvent.

| compound | melting point °C. | compound | melting point °C. |
| --- | --- | --- | --- |
| (2) | 199–202 | (38) | 104 |
| (5) | 139–141 | (39) | oil |
| (7) | 118 | (40) | 152 |
| (9) | 102 | (43) | 179–184 |
| (11) | 80 | (44) | 143–144 |
| (13) | 55–57 | (46) | oil; $R_f(Et_2O)$ 0.2 |
| (15) | 64–67 | (47) | oil; $R_f(Et_2O)$ 0.5 |
| (18) | 120 | (49) | 62–64 |
| (20) | 76–79 | (52) | oil; $R_f(Et_2O)$ 0.5 |
| (22) | 55–57 | (54) | oil; $R_f(Et_2O)$ 0.4 |
| (24) | 62–65 | (57) | 129–132 |
| (28) | 130–132 | (58) | 93–96 |
| (32) | 71 | (59) | 97–98 |
| (34) | 73 | (60) | oil; $R_f(Et_2O)$ 0.25 |
| (37) | 230 (decomp.) | | |

EXAMPLE II

Preparation of 2-n-butylsulphonyl-4-amino-5-cyanothiazole (6)

9.0 g of 85% m-chloroperbenzoic acid are added in portions to a solution of 4.26 g of 2-n-butylthio-4-amino-5-cyanothiazole in 200 ml of methylene chloride, while stirring and at room temperature. After stirring overnight at room temperature an excess of sodium bicarbonate in water is added and the solution is stirred for one hour. The organic layer is separated, washed with water, dried, filtered and diluted with isopropanol. After distilling off a part of the methylene chloride the desired product crystallises: yield 4.34 g; melting-point 150°–152° C.; TLC: $R_f(CH_2Cl_2)$ 0.05.

The following compounds are prepared in a corresponding manner:

| compound | melting point °C. | compound | melting point °C. |
| --- | --- | --- | --- |
| (1) | 207–211 (decomp.) | (30) | 137 |
| (3) | 150 | (31) | 134–137 |
| (4) | 150–156 | (33) | 80–82 |
| (8) | 159 | (35) | 101–102 |
| (10) | 88–91 | (36)* | 167–169 |
| (12) | 75 | (41) | 114–117 |
| (14) | 48–51 | (42) | 173–175 |
| (16) | 57–60 | (45) | oil; $R_f(Et_2O)$ 0.35 |
| (19) | 54–57 | (48) | oil; $R_f(CH_2Cl_2)$ 0.35 |
| (21) | 59–60 | (50) | 58–61 |
| (23) | 55–58 | (51) | 92–94 |
| (25) | 128 | (53) | 69–71 |
| (26) | 92 | (55) | 42–44 |
| (27) | 114–117 | (56) | 84–86 |
| (29) | oil; $R_f(Et_2O)$ 0.4 | (61) | 114–116 |

(*)from 2-n-butylthio-4-phenylthio-5-cyanothiazole; with a four-fold molar quantity of m-chloroperbenzoic acid.

EXAMPLE III

Preparation of 2-n-butylthio-4-amino-5-cyanothiazole, starting substance for the preparation of compounds (6) and (7) according to examples I and II A concentrated solution of 128 g of KOH in approximately 80 ml of water is slowly added dropwise to a solution of 42.0 g of cyanamide in approximately 500 ml of dimethyl formamide to which 90 ml (114 g) of carbon disulphide have been added. During the addition the mixture is stirred and kept at a temperature of 0°–10° C. by cooling. After 45 minutes, 107 ml (137 g) of n-butylbromide are slowly added dropwise while cooling and stirring and, after 30 minutes, 63.5 ml (75.5 g) of chloroacetonitrile are then added. The cooling bath is removed and, after stirring for another 30 minutes, a concentrated solution of 10 g of KOH in water is added, the temperature of the reaction mixture rising to approximately 60° C. After stirring for another hour at 60° C. the reaction mixture is poured in 2.5 l of ice water, after which the formed precipitate is sucked off, washed successively with water, isopropyl alcohol and petroleum ether, and dried. The desired product is obtained in a yield of 158.9 g and melts at 115°–117° C.

The following compounds are prepared in a corresponding manner:

2-ethylthio-4-amino-5-cyanothiazole, used for the preparation of compound (3) according to example II;

2-methylthio-4-amino-5-cyanothiazole, used for the preparation of compounds (1) and (2) according to examples I and II;

2-n-propylthio-4-amino-5-cyanothiazole, starting substance for the preparation of compounds (4) and (5) according to examples I and II;

2-n-hexylthio-4-amino-5-cyanothiazole, starting substance for the preparation of compounds (8) and (9) according to examples I and II; and 2-cyanomethylthio-4-amino-5-cyanothiazole, starting substance for the preparation of compound (37) according to example I.

EXAMPLE IV (a) Preparation of 2-n-butylthio-4-amino-5-acetylthiazole, starting substance for the preparation of compounds (31) and (32) according to examples I and II The title compound is prepared in the same manner as described in Example III, with the proviso that for the ring closure reaction 84 ml (92.5 g) of chloroacetone instead of chloroacetonitrile are used. 2-n-Butylthio-4-amino-5-acetylthiazole is obtained in a yield of 169.3 g; melting-point 79°–81° C.

In a corresponding manner the following compounds are prepared:

2-ethyl-4-amino-5-acetylthiazole, starting substance for the preparation of compounds (30) and (44) according to examples I and II; and 2-n-hexylthio-4-amino-5-acetylthiazole, starting substance for the preparation of compounds (33) and (34) according to examples II and I;

(b) Preparation of 2-n-butylthio-4-amino-5-benzoylthiazole, starting substance for the preparation of compounds (38) and (51) according to examples I and II The title compound is prepared in the same manner as described in example III, with the proviso that 199 g of phenacyl bromide are used for the ring closure reaction instead of chloro acetonitrile; yield 206.6 g; m.p. 91°–94° C.

2-Hexylthio-4-amino-5-benzoylthiazole is prepared in a corresponding manner.

(c) Preparation of 2-methylthio-4-amino-5-formylthiazole

The title compound is prepared in the same manner as described in example III, with the proviso that 62.4 ml of methyliodide are used for the alkylation instead of n-butyl bromide and 130 ml of chloroacetaldehyde (approximately 50% solution in water) are used instead of chloroacetonitrile for the ring closure reaction; yield 97.3 g; m.p. 159°–162° C.

EXAMPLE V (a) The thiazoles unsubstituted in the 4-position and required for the preparation of the compounds (10), (11), (12), (13), (14), (15), (16), (17), (49), (50), (54), (55) and (59), mentioned in Examples I and II, are prepared as follows from the 4-aminothiazoles obtained according to examples III and IV:

Preparation of 2-N-butylthio-5-cyanothiazole 21.3 g Of 2-n-butylthio-4-amino-5-cyanothiazole obtained according to Example III are added in portions while stirring to a solution of 28 ml (24.7 g) of isoamyl nitrite in 280 ml of dimethyl formamide at 60° C. Stirring is continued for another 30 minutes at a temperature of 65°–70° C. and the reaction mixture is then evaporated. The residue is taken up in methylene chloride. The solution is washed twice with a saline solution, dried and decoloured with charcoal. After the addition of isopropanol and evaporating methylene chloride, the crystalline product is sucked off. The desired compound is obtained in a yield of 11.95 g; melting-point 38°–41° C.; $R_f(CH_2Cl_2)$ 0.35.

(b) The 4-chlorothiazoles required for the preparation of the compounds (18), (19), (20), (21), (22), (23), (24), (39), (41), (47), (48), (52), (53), (58) and (61), mentioned in examples I and II, are prepared as follows from the 4-aminothiazoles obtained according to examples III, IV and VII.

Preparation of 2-methylthio-4-chloro-5-cyanothiazole

A concentrated solution of 42 g of sodium nitrite in water is slowly added dropwise to a mixture of 68.4 g of 2-methylthio-4-amino-5-cyanothiazole, obtained according to example III, 100 ml of water, 300 ml of concentrated hydrochloric acid, 70 g of cuprous chloride ($CuCl_2.2H_2O$) and 800 ml of methylene chloride while stirring and cooling at approximately 0° C. After stirring for another 30 minutes at 0°–5° C. the mixture is diluted with water. The reaction mixture is filtered off and the filtrate is separated; the organic layer is washed with water, dried, filtered and evaporated while adding isopropanol until crystallisation. The desired compound is obtained in a yield of 46.3 g; m.p. 83°–87° C.

The above-mentioned compounds can be prepared in a different manner as follows:

60 ml Of isoamylnitrite and portionwise 46.0 g of 2-n-butylthio-4-amino-5-acetylthiazole, obtained according to example IV, are successively added to a mixture of 40.35 g of anhydrous $CuCl_2$ and 400 ml of dry acetonitrile while stirring and heating at approx. 65° C. After stirring for another hour at 65° C. and evaporating, the residue is taken up in a mixture of methylene chloride and 6N hydrochloric acid. The organic layer is separated, washed with a saline solution, dried and filtered. After chromatographing the methylene chloride solution over a 5 l dry silica gel column, 2-n-butylthio-4-chloro-5-acetylthiazole is obtained in a yield of 31.5 g; oil; TLC: $R_f(CH_2Cl_2)$ 0.4.

(c) Preparation of 2-n-butylthio-4-N-acetylamino-5-cyanothiazole, starting substance for the preparation of compounds (27) and (28) according to examples II and I.

80 ml Of acetic acid anhydride are slowly added dropwise at 60° C. whilde stirring to a mixture of 21.3 g of 2-n-butylthio-4-amino-5-cyanothiazole, obtained according to example III, 3 g of p-N,N-dimethylaminopyridine as a catalyst, 300 ml of acetonitrile and 20 ml of triethyl amine. After stirring for another 5 hours at 60° C. the reaction mixture is evaporated, after which the residue is dissolved in approximately 200 ml of ethanol. After evaporating, the resulting residue is dissolved in approximately 200 ml of isopropanol, decoloured with charcoal and made to crystallise in the refrigerator. The desired product is obtained in a yield of 16.3 g; m.p. 95°–99° C.; $R_f(CH_2Cl_2)$ 0.1.

The following compounds are prepared in a corresponding manner:

2-methylthio-4-N-acetylamino-5-cyanothiazole, starting substance for the preparation of compound (40) according to example I;

2-n-butylthio-4-N-acetylamino-5-acethylthiazole, starting substance for the preparation of compound (56) according to example II; and 2-n-propylthio-4-N-acetylamino-5-cyanothiazole, starting substance for the preparation of compound (60) according to examples V(e) and I.

(d) Preparation of 2-ethylthio-4-N-methoxycarbonylamino-5-cyanothiazole, starting substance for the preparation of compound (25) according to example II.

2-Ethylthio-4-amino-5-cyanothiazole, prepared according to example III, is suspended in a quantity of 18.5 g in 400 ml of acetonitrile, to which 30 ml of triethylamine have been added. After the addition of 2 g of p-N,N-dimethylaminopyridine as a catalyst, a solution of 30 g of dimethylpyrocarbonate in 100 ml of acetonitrile is added portionwise at approximately 40° C. while shaking. After heating at approximately 50° C. for 1 hour the reaction mixture is filtered over charcoal and evaporated to dryness. After the addition of 5 ml of acetic acid, the residue is taken up in a mixture of 500 ml of water and 150 ml of 2N sodium hydroxide solution. After filtering and acidifying with acetic acid, the precipitated solid is sucked off, washed with water and taken up in methylene chloride. The organic solution, after drying, filtering and evaporating the solvent, provided the title compound in a yield of 10 g, m.p. 116° C.

(e) Preparation of 2-n-butylthio-4-(N-methyl-N-acetylamino)-5-cyanothiazole, starting substance for the preparation of compounds (29) and (46) according to examples II and I.

8.0 ml (18.2 g) of methyl iodide are added dropwise while stirring at 60° C. to a mixture of 15.3 g of 2-n-butylthio-4-N-acetylamino-5-cyanothiazole obtained according to example V(c), 10,0 g of potassium carbonate and 300 ml of acetonitrile. After stirring at 60° C. for 3 hours again the same quantity of methyl iodide is added; this is repeated a few times at 45° C. and 40° C. The reaction product is worked up by dissolving in methylene chloride, washing with water, drying, filtering, evaporating, dissolving in diethyl ether and chromatographing over a 1600 ml dry silica gel column. The desired compound is obtained as an oil in a yield of 11.0 g; $R_f(Et_2O)$ 0.45.

In a corresponding manner 2-n-propylthio-4-(N-acetyl-N-propargylamino)-5-cyanothiazole is prepared, starting substance for the preparation of compound (60) according to example I.

(f) The methylation may be carried out in a manner differing from that described sub V(e).

A mixture of 14.56 g of 2-ethylthio-4-N-methoxycarbonylamino-5-cyanothiazole, obtained according to example V(d), 4 g of powdered KOH, 2 ml of triethyl amine and 12 g of methyl iodide is stirred at room temperature in 250 ml of acetonitrile for 1 hour and is then refluxed at 40° C. for another 2 hours. After the addition of 100 ml of diethyl ether and decanting, the solution is evaporated. The residue is taken up in petroleum ether, after which the desired product crystallises in the refrigerator. The resulting 2-ethylthio-4-(N-methyl-N-methoxycarbonylamino)-5-cyanothiazole, starting substance for the preparation of compound (26) according to example II, is isolated in a yield of 14.6 g; m.p. 40° C.

EXAMPLE VI

(a) Preparation of 2-n-butylthio-4-phenoxy-5-cyanothiazole, starting substance for the preparation of compound (35) according to example II.

Phenol in a quantity of 4.7 g is dissolved in 50 ml of methanol in which 1.15 g of sodium has been dissolved. After the addition of 50 ml of dimethyl formamide the methanol is evaporated. The remaining solution is added, while stirring and cooling with ice, to a solution of 11.63 g of 2-n-butylthio-4-chloro-5-cyanothiazole, prepared according to example V(b), in 100 ml of acetonitrile. After refluxing for 2 hours the acetonitrile is evaporated and the residue is diluted with ice water. The organic phase is extracted with methylene chloride, after which the methylene chloride solution is separated, washed with 1N sodium hydroxide solution, again with water, dried and evaporated. The residue is taken up in diisopropyl ether and filtered, after which the solvent is again distilled off from the filtrate. After taking up in a mixture of petroleum ether (40–60) and diethyl ether (3:1 v/v) the residue is chromatographed over a 1 l dry silica gel column. The desired compound is obtained in a yield of 4.57 g; $R_f$(petr.ether/diethyl ether 3:1) 0.4; oil; characterized by means of I.R. spectrum.

In a corresponding manner from 2-n-butylthio-4-chloro-5-cyanothiazole and sodium methoxide is prepared 2-n-butylthio-4-methoxy-5-cyanothiazole, starting substance for the preparation of compound (45) according to example II.

(b) Preparation of 2-n-butylthio-4-phenylthio-5-cyanothiazole, starting substance for the preparation of compound (36) according to example II.

5.15 ml (5.55 g) of thiophenol and 7.0 ml of triethylamine are added successively while stirring to a solution of 10.93 g of 2-n-butylthio-4-chloro-5-cyanothiazole prepared according to Example V(b), in 100 ml of acetonitrile. After stirring at room temperature for another hour and leaving to stand overnight, the reaction mixture is evaporated. The residue is dissolved in methylene chloride, after which the organic solution is successively washed with water, 1N sodium hydroxide solution and water, and is then dried, filtered and evaporated. Chromatography in petroleum ether (40–60)-/diethyl ether 3:1 v/v as a solvent over a 1400 ml dry silica gel column provides the desired product in a yield of 7.24 g; oil; $R_f$(petr.ether/diethyl ether 3:1 v/v) 0.35; identification by means of I.R. spectrum.

(c) Preparation of 2-methylthio-4-(8-quinolyloxy)-5-cyanothiazole, starting substance for the preparation of compound (57) according to example I.

A quantity of 1.15 g of sodium is dissolved in 50 ml of methanol. After the addition of a solution of 7.25 g of 8-hyroxyquinoline in 50 ml of dimethyl formamide the methanol is evaporated. A solution of 9.53 g of 2-methylthio-4-chloro-5-cyanothiazole, obtained according to example V (b) is added to this solution while stirring and cooling. After heating at approximately 100° C. for 7 hours the reaction mixture is poured in 0.5 l of ice water. The formed precipitate is sucked off, washed with water and taken up in methylene chloride. After drying, filtering with charcoal, diluting with ethanol and evaporating the methylene chloride, the title compound crystallises in a yield of 7.69 g; m.p. 139°–142° C.; TLC: $R_f$(Et$_2$O) 0.35.

EXAMPLE VII

Preparation of 2-phenylthio-4-amino-5-cyanothiazole, starting substance for the preparation of compounds (42) and (43) according to examples II and I.

15.5 ml (16.5 g) of thiophenol are added to a suspension of 9.35 g of 2-methylsulphinyl-4-amino-5-cyanothiazole, prepared according to example I, in 250 ml of acetonitrile, while stirring. After stirring at room temperature for another 30 minutes and leaving to stand overnight, the mixture is filtered with charcoal, after which the filtrate is evaporated. The residue is taken up in methylene chloride, after which the resulting solution is washed, successively with 2N sodium hydroxide solution and water, dried, filtered and diluted with isopropanol. After evaporating the methylene chloride the desired product crystallises in a yield of 7.62 g; m.p. 176°–18° C.; $R_f$(CH$_2$Cl$_2$) 0.15.

EXAMPLE VIII (a) Preparation of a solution of an active substance, viz. 2-ethylsulphinyl-4-chloro-5-cyanozole (20), in a water-miscible liquid ("liquid").

10 g of the above active substance are dissolved in a mixture of 10 ml of isophorone and approximately 70 ml of dimethyl formamide, after which a quantity of 10 g of polyoxyethylene glycol ricinyl ether are added as an emulsifier.

In a corresponding manner the other active substances are processed to 10 or 20% "liquids".

In a corresponding manner liquids are obtained in N-methyl pyrrolidone, dimethyl formamide, and a mixture of N-methyl pyrrolidone and isophorone as solvents.

(b) Preparation of a solution of the active substance in a organic solvent.

200 mg of the active substance to be examined are dissolved in 1000 ml of acetone in the presence of 1.6 g of nonylphenolpolyoxyethylene. This solution, after pouring in water, may be used as a spray liquid.

(c) Preparation of an emulsifiable concentrate of the active substance.

10 g of the active substance to be examined are dissolved in a mixture of 15 ml of isophorone and 70 ml of xylene; 5 g of a mixture of a polyoxyethylene sorbitan ester and an alkylbenzene sulphonate are added to this solution as an emulsifier.

(d) Preparation of a dispersible powder (W.P.) of the active substance.

25 g of the active substance to be examined are mixed with 68 g of kaolin in the presence of 2 g of sodium butylnaphthalene sulphonate and 5 g of lignine sulphonate.

(e) Preparation of a suspension concentrate (flowable) of the active substance.

A mixture of 10 g of active substance, 2 g of lignine sulphonate and 0.8 g of a sodium alkyl sulphate is made up with water to an overall quantity of 100 ml.

(f) Preparation of a granule of the active substance.

7.5 g of active substance, 5 g of sulphite lye and 87.5 g of ground dolomite are mixed, after which the resulting mixture is processed to a granular composition.

EXAMPLE IX

Test with respect to the protection of seedlings against a plant pathogenic seed fungus, viz. *Fusarium culmorum*, by means of a seed treatment.

Wheat seed, seriously infested with *Fusarium culmorum*, is treated with the substance to be tested in the form of a composition in a quantity of 3 g per kg of seed. The composition is obtained by pulverising the substance to be tested and then intimately mixing with kaolin in a concentration of 10% by weight. The seed thus treated is sown in a tray containing soil which is placed in a Wisconsin tank with a bottom temperature of 8°–12° C. After 2 weeks the number of emerged and healthy plants is determined. The emergence of healthy plants from untreated seed serves as control. For comparison, the known substance 2-methylsulphinyl-4-methyl-5-nitrothiazole mentioned hereinbefore are also tested. The results are recorded in Table A below. In the examples, the numbers of the compounds refer to the specification.

TABLE A

| Compound No. | Percentage of emerged, healthy plants |
|---|---|
| (18) | 77 |
| (20) | 83 |
| (32) | 88 |
| (34) | 80 |
| known | 62 |
| untreated | 39 |

EXAMPLE X

Test with respect to the protection of seedlings against a plant-pathogenic soil fungus, viz. Pythium spp., by means of a seed treatment.

The compounds to be tested are processed to compositions by pulverising them and then mixing them intimately with kaolin in the desired concentration (see Table B). Beet seed is treated with these compositions in a quantity of 6 g of composition per kg of seed and then sown in trays with soil which is seriously infested with Pythium spp. After 2 weeks in a glass-house at 18°-22° C. and a relative humidity of 70-100%, the percentage of non-emerged and diseased seedlings (% damping-off) is determined. The results are recorded in Table B. For comparison, the known substance 2-methylsulphinyl-4-methyl-5-nitrothiazole is also tested.

TABLE B

| Compound No. | Dosage in mg of active substance per kg of seed | percentage damping-off |
|---|---|---|
| (11) | 600 | 18 |
|  | 1200 | 21 |
| (18) | 600 | 14 |
|  | 1200 | 17 |
| (20) | 600 | 9 |
|  | 1200 | 14 |
| known | 600 | 69 |
|  | 1200 | 62 |
| untreated | — | 91 |

EXAMPLE XI

Test with respect to the protection of seedlings aginst a plant pathogenic seed fungus, viz. Leptosphaeria nodorum, by means of a seed treatment.

Wheat seed, seriously infested with Leptosphaeria nodorum, is treated with the substance to be tested in the form of 10% and 20% compositions in quantities of 3 g per kg of seed. The compositions are obtained by pulverising the substance to be tested and then initimately mixing with kaolin in concentrations of 10 and 20% by weight, respectively. The seed thus treated is sown and treated as described in example IX. After 3 weeks the number of infested plants is determined and compared with that of untreated seed. The results are recored in Table C hereinafter.

TABLE C

| Compound No. | Dosage in mg of active substance per kg of seed | percentage of diseased plants |
|---|---|---|
| (11) | 300 | 9 |
|  | 600 | 0 |
| (18) | 300 | 4 |
|  | 600 | 1 |
| (20) | 300 | 2 |
|  | 600 | 0 |
| (32) | 300 | 7 |
|  | 600 | 1 |
| (34) | 300 | 17 |
|  | 600 | 7 |
| untreated | — | 52 |

EXAMPLE XII

Field test with respect to the protection of seedlings against Fusarium culmorum by means of a seed treatment.

Seed of winter wheat, seriously infested with Fusarium culmorum, is treated with the substance to be tested in the form of 10% and 20% compositions in quantities of 2 g per kg of seed. The compositions are obtained as described in example XI. The seed thus treated is sown in the open air in rows of 2 meters length; each test is repeated four times. After 5 weeks the number of emerged and the number of healthy plants are determined. The emergence of healthy plants from untreated seed serves as a control. For comparison, the known substance 2-methylsulphinyl-4-methyl-5-nitrothiazole is also tested. As a standard treatment is used a treatment with the standard agent Panoctine ® 35, a 35% composition on the basis of guatazine triacetate, in a quantity of 2 ml per kg of seed. The average emergence of the plants and the effectiveness with respect to the standard treatment (=100) are recorded in Table D below.

TABLE D

| Comp. no. | dosage in mg of active substance per kg of seed | average emergence | effectiveness with respect to standard treatment |
|---|---|---|---|
| (18) | 200 | 120 | 101 |
|  | 400 | 137 | 115 |
| (20) | 200 | 125 | 105 |
|  | 400 | 140 | 118 |
| (32) | 200 | 120 | 101 |
|  | 400 | 134 | 113 |
| known | 200 | 109 | 92 |
|  | 400 | 101 | 85* |
| Panoctine 35 | 700 | 119 | (100) |
| untreated | — | 104 | 87 |

*significant phytotoxicity observed

EXAMPLE XIII

Test on activity against leaf fungi.

The active substances to be tested are processed to aqueous suspensions as described in example VIII (e). The crop to be protected against false mildew on tomato (Phytophthora infestans) is treated with these compositions by spraying young tomato plants of approximately 10 cm high with the above suspensions of the active substances in a concentration of 300 mg of active substance per liter. The plants thus treated are then infected with Phytophthora infestans by spraying the plants with an aqueous suspension containing per ml 100,000 spores of Phytophthora infestans. After an incubation period of 4 days at a temperature of approximately 18° C. and a relative humidity of 100% it is determined so what extent the fungus has developed. During the incubation period a light/dark cycle of 16/8 hours is maintained. The tested compound No. (5), (6), (7), (8), (9), (56), (57), (60) and (61) provide a protection against fungus infestation of at least 90%, the known compound 2-methylsulphinyl-4-methyl-5-nitrothiazole, mentioned hereinbefore, does not give any protection.

EXAMPLE XIV

In vitro test on activity against Leptosphaeria nodorum.

The compound to be tested is incorporated into a culture medium consisting of 1% by weight of glucose, 0.2% by weigh of a yeast extract (marmite), 0.5% by weight of a protein (pepton), 2.5% by weight of agar-agar and 95.8% by weight of water, in petri dishes in concentrations of 10 and 30 ppm. The petri dishes are inoculated with the plant pathogenic fungus Leptosphaeria nodorum and are then kept at a temperature of 22° C. After 5 days the growth inhibiting activity of the compounds is visually determined. For comparison, the known compound 2-methylsulphinyl-4-methyl-5-nitrothiazole, mentioned hereinbefore, has also been tested. The results are recorded in Table E.

TABLE E

| comp. no. | conc. in ppm. | % of growth inhibition of the fungus |
|---|---|---|
| (7) | 10 | 63 |

TABLE E-continued

| comp. no. | conc. in ppm. | % of growth inhibition of the fungus |
| --- | --- | --- |
|  | 30 | 80 |
| (9) | 10 | 71 |
|  | 30 | 89 |
| (11) | 10 | 53 |
|  | 30 | 84 |
| (13) | 10 | 86 |
|  | 30 | 95 |
| (18) | 10 | 60 |
|  | 30 | 96 |
| (20) | 10 | 84 |
|  | 30 | 100 |
| (24) | 10 | 49 |
|  | 30 | 92 |
| (32) | 10 | 70 |
|  | 30 | 100 |
| (34) | 10 | 63 |
|  | 30 | 100 |
| (38) | 10 | 52 |
|  | 30 | 83 |
| known | 10 | 28 |
|  | 30 | 43 |
| control | — | 0 |

EXAMPLE XV

Compounds according to the invention are tested on *Fusarium culmorum* in the same manner as described in example XIV. The following compounds cause at least 75% growth inhibition of fungus in a concentration of 30 ppm.: (9), (10), (11), (12), (13), (16), (17), (18), (19), (20), (22), (24), (32), (34), (38), (44) and (47).

EXAMPLE XVI

Compounds according to the invention are tested on *Pyrenophora graminea* in the same manner as described in example XIV. The following compounds cause at least 75% growth inhibition of the fungus in a concentration of 30 ppm.: (3), (4), (5), (6), (8), (10), (11), (12), (13), (14), (15), (16), (18), (20), (22), (23), (24), (32), (33), (34), (38), (44), (45), (47), (48), (49), (50), (52), (53), (54) and (55).

EXAMPLE XVIII

Compounds according to the invention are tested on *Pythium splendens* in the same maner as described in example XIV. The following compounds cause at least 90% growth inhibition of the fungus in a concentration of 10 ppm.: (1), (2), (3), (4), (5), (6), (7), (8), (10), (11), (12), (13), (14), (15), (16), (17), (18), (19), (20), (21), (22), (24), (27), (28), (32), (33), (34), (37), (38), (42), (43), (44), (46), (47), (48), (49), (50), (56), (57), (58) and (59).

EXAMPLE XVIII

Compounds according to the invention are tested on *Rhizoctonia solani* in the same manner as described in example XIV. The following compounds cause at least 50% growth inhibition of the fungus in a concentration of 30 ppm.: (3), (6), (8), (9), (10), (11), (12), (14), (15), (16), (17), (18), (19), (20), (21), (22), (23), (24), (32), (33), (34), (38), (39), (41), (42), (43), (44), (45), (46), (47), (48), (49), (50), (51), (52), (53), (54), (55), (57), (59) and (61).

We claim:

1. Thiazole compounds of the general formula

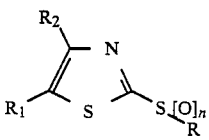

(I)

wherein

R is $C_1-C_{12}$ alkyl group or a phenyl group;

$R_1$ is a cyano group, a formyl group, an alkylcarbonyl group having 2-5 carbon atoms, or a benzoyl group;

$R_2$ is a hydrogen atom; a halogen atom; an amino group; an amino group substituted with 1 or 2 substituents selected from the group consisting of $C_1-C_4$ alkyl, $C_2-C_5$ alkynyl, $C_2-C_5$ alkylcarbonyl and $C_2-C_5$ alkoxycarbonyl; an alkoxy group having 1-4 carbon atoms; or an aryloxy or arylsulphonyl group, wherein the aryl group is selected from phenyl and quinolyl; and n is 1 or 2.

2. Compounds as claimed in claim 1 of the general formula

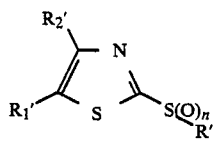

(II)

wherein

R' is an alkyl group having 1-6 carbon atoms, $R_1'$ is a cyano group or an acetyl group, $R_2'$ is a hydrogen atom, a halogen atom, an amino group, or an amino group substituted with 1 or 2 substituents selected from the group consisting of $C_1-C_4$ alkyl, $C_2-C_5$ alkylcarbonyl and $C_2-C_5$ alkoxycarbonyl, and n is 1 or 2.

3. A fungicidal compositions, characterized in that, in addition to a liquid or solid carrier material, the composition comprises a fungicidally effective amount compound of the general formula I, wherein the symbols have the meanings given in claim 1.

4. A composition for the treatment of soil or seed against phytophagous micro-organisms, characterized in that, in addition to a liquid or solid carrier material, the composition comprises a fungicidally effective amount compound of the general formula I, wherein the symbols have the meanings given in claim 1.

5. A composition as claimed in claim 3 or 4, characterized in that the active constituent is a compound of the general formula II, wherein the symbols have the meanings given in claim 2.

6. A method of preventing or controlling fungus infections in agriculture and horticulture, characterized in that the crop to be protected or the infested crop is treated with a composition as claimed in claim 3 in a dosage from 250 to 1,000 g of active substance per hectare.

7. A method of preventing infections by phytophagous micro-organisms in agriculture and horticulture, characterized in that the soil destined for sowing or planting is treated with a composition as claimed in claim 4 in a dosage from 2 to 100 kg of active substance per hectare, or that the seed, before sowing, is treated with a composition as claimed in claim 4 in a dosage from 100 to 1,500 mg of active substance per kg of seed.

8. A method of preventing or controlling fungus infections in agriculture and horticulture, characterized in that the crop to be protected or the infested crop is treated with a composition as claimed in claim 5 in a dosage from 250 to 1,000 g of active substance per hectare.

9. A method of preventing infections by phytophagous micro-organisms in agriculture and horticulture, characterized in that the soil destined for sowing or planting is treated with a composition as claimed in claim 5 in a dosage from 2 to 100 kg of active substance per hectare, or that the seed, before sowing, is treated with a composition as claimed in claim 5 in a dosage from 100 to 1,500 mg of active substance per kg of seed.

* * * * *